United States Patent [19]
Yachia et al.

[11] Patent Number: 4,602,625
[45] Date of Patent: Jul. 29, 1986

[54] PENILE ERECTILE SYSTEM

[75] Inventors: Daniel Yachia, Ramat Efal, Israel; Henry W. Lynch, Racine, Wis.

[73] Assignee: Medical Engineering Corporation, Racine, Wis.

[21] Appl. No.: 705,052

[22] Filed: Feb. 22, 1985

Related U.S. Application Data

[63] Continuation-in-part of Ser. No. 472,155, Mar. 4, 1983, Pat. No. 4,523,584.

[51] Int. Cl.⁴ .................................................. A61F 5/00
[52] U.S. Cl. ...................................................... 128/79
[58] Field of Search .......................................... 128/79

[56] References Cited

U.S. PATENT DOCUMENTS

| | | | |
|---|---|---|---|
| 4,201,202 | 5/1980 | Finney et al. | 128/79 |
| 4,204,530 | 5/1980 | Finney | 128/79 |
| 4,281,648 | 8/1981 | Rogers | 128/79 |
| 4,369,771 | 1/1983 | Trick | 128/79 |
| 4,407,275 | 10/1983 | Schroeder | 128/79 |
| 4,523,584 | 6/1985 | Yachia et al. | 128/79 |

FOREIGN PATENT DOCUMENTS 835637 7/1949 Fed. Rep. of Germany ........ 128/79

*Primary Examiner*—Dalton L. Truluck
*Attorney, Agent, or Firm*—Quarles & Brady

[57] ABSTRACT

A penile erectile system for treating male impotency comprises a sleeve of biocompatible material having at least one pressurizable chamber which is adapted to be implanted about the penile shaft of a patient beneath the penile skin between the skin and the shaft and a body member integrally attached to said sleeve. The body member comprising a fluid reservoir for pressurizing fluid, and a pump for transferring the fluid under pressure from the reservoir to the chamber.

8 Claims, 6 Drawing Figures

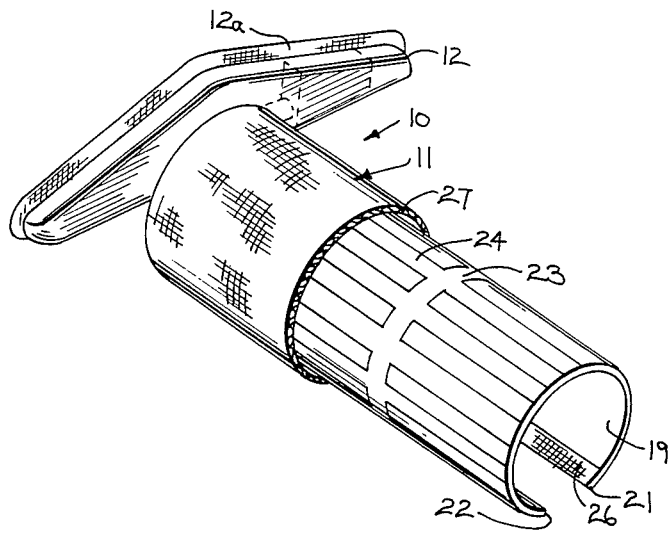

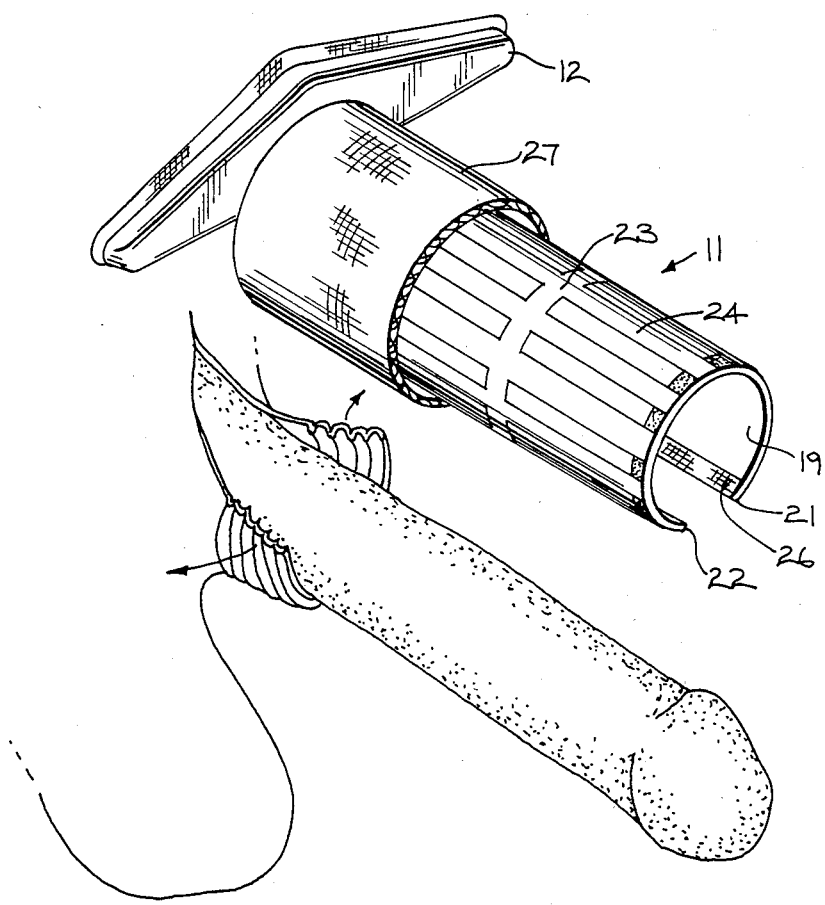
FIG. 4
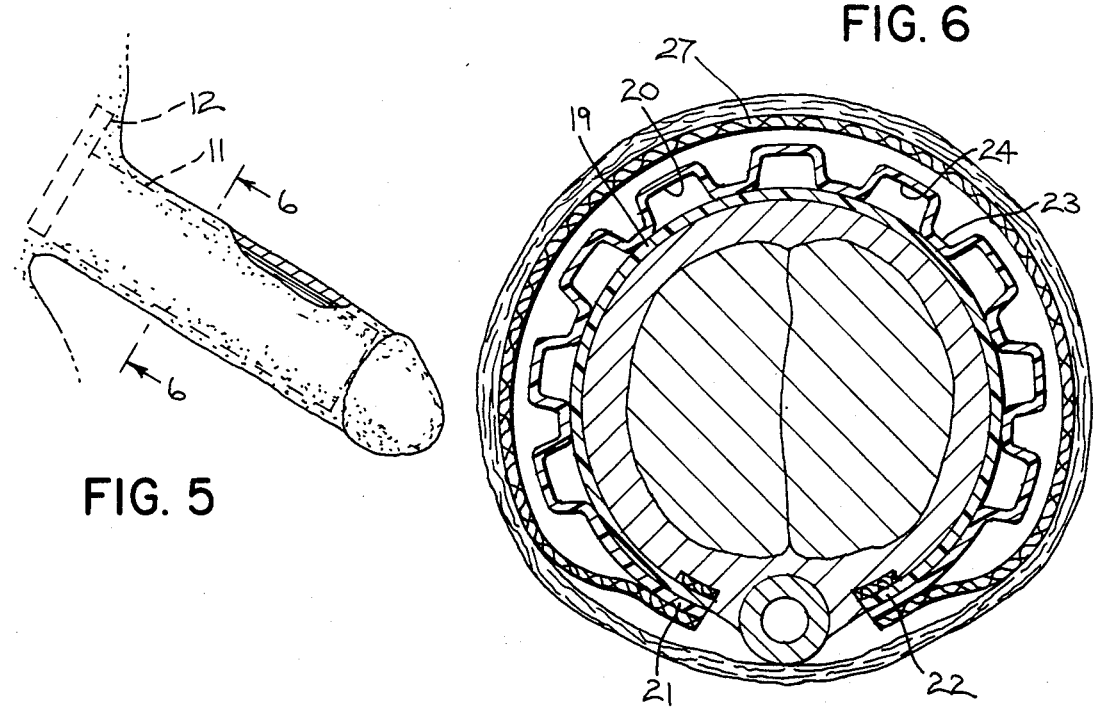
FIG. 5
FIG. 6

PENILE ERECTILE SYSTEM

RELATED CASE

The present application is a continuation-in-part of our earlier copending application Ser. No. 472,155 filed Mar. 4, 1983, now U.S. Pat. No. 4,523,584 issued June 18, 1985.

FIELD OF THE INVENTION

The present invention relates to a penile erectile system. More particularly, it relates to an inflatable, implantable penile erectile system.

DESCRIPTION OF THE PRIOR ART

There are some cases of erectile impotence for which the surgical implantation of a penile erectile system is the only practical means of remedying the impotency. In such cases in the past, several different types of implantable penile erectile systems have been employed.

One type of implantable penile erectile system which has been used is an inflatable system which includes two inflatable and distensible tubes each of which is surgically implanted in a separate corpus cavernosum of the penis. Each of the tubes is connected by tubing to a relatively large reservoir of inflating and pressurizing fluid which is implanted elsewhere in the body. An erection is achieved by inflating and pressurizing the distensible tubes. The devices of Buuck U.S. Pat. No. 3,954,102 and Uson U.S. Pat. No. 4,009,711 are representative of inflatable penile erectile systems.

Another type of penile erectile system comprises a pair of rods of suitable stiffness which are surgically implanted into the corpora cavernosa of the penis. A significant advantage of this system is that the amount of surgery involved is minimal as there is no fluid reservoir to implant. A disadvantage of this system is that the permanent stiffness of the rods can be a source of physical pain and embarrassment to the patient. Representative penile erectile systems employing rod implants are disclosed in Small et al. U.S. Pat. No. 3,893,456 and Finney et al. U.S. Pat. No. 4,066,037.

Another implantable erectile system which combines some of the features of both the inflatable system and the rod-type system is disclosed in Finney U.S. Pat. No. 4,201,202. The system disclosed therein includes a rod within a sleeve positioned about the rod to form a chamber. An erection is achieved by pressurizing the chamber with fluid to make it stiff and thus to straighten and support the rod. The chamber is depressurized by use of a pressure control valve.

A common disadvantage of all of the foregoing systems is that in each of them either tubes or rods are implanted into the corpora cavernosa replacing the spongy tissue and thus making the operation irreversible.

SUMMARY OF THE INVENTION

It is the general object of the present invention to disclose a novel implantable penile erectile system.

It is a further object to disclose a novel implantable penile erectile system which can be implanted without replacing the spongy tissue essential for a normal erection.

The penile erectile system of the present invention consists of a pressurizable sleeve which can be surgically implanted around the penile shaft under the penile skin, between the penile shaft and the skin, a reservoir for pressurizing fluid, a pump, and valve means for controlling the flow of fluid to the sleeve.

In the preferred embodiment of the present invention, the sleeve is preferably comprised of two layers of a biocompatible material, such as silicone rubber, which are sealed together along their borders to form at least one pressurizable chamber. To achieve even inflation and rigidity, the layers are preferably further sealed within their borders to form a plurality of divided, longitudinal chambers which are interconnected by a manifold.

In one embodiment, the layer is material forming the outer layer is elastic and distensible and the layer forming the inner surface, when the sleeve is placed about the penile shaft, is of a higher modulus, stiffer and less elastic material. When this embodiment is pressurized the outer layer stretches or distends outwardly so that the sleeve causes an expansion in the girth of the penis, as well as a stiffening of the shaft.

The sleeve can be supplied in various shapes and sizes. The sleeve selected for use in a patent should be long enough to extend from the arcuate pubic ligament of the patient to the corona of the glans and of a width sufficient to cover the corpora cavernosa. In order to manimize buckling on the underside when the penis is flaccid, the width of the sleeve does not cover the urethra. To keep the sleeve in place, the two longitudinal sides of the sleeve also may be joined together by mesh, webbing or single layer of membrane. When a single layer membrane is used to join the two longitudinal sides of the sleeve, it is preferred to use a very low modulus (stretchy) high elongation material. When the low modulus membrane is attached to the sides of the sleeve the membrane should be stretched longitudinally about 50% so that in repose it will pull the sleeve into a normal pendant position, without wrinkling or folding. Alternatively, the longitudinal sides of the sleeve may be provided with suture tabs or other anchoring means.

The penile erectile system of the present invention also includes a reservoir for pressurizing fluid, a pump, valve means which opens to permit pressurizing fluid into the chamber of the sleeve and then closes to retain the fluid in the chamber, and a pressure relief valve for depressurizing the chamber and to permit the pressurizing fluid to return to the reservoir. The various components of the system of the present invention are joined together in a leakproof manner to form a closed hydraulic system.

In our earlier application we described an implant in which the pump and reservoir were connected to the sleeve by tubing so that they could be implanted in the scrotum. In the present invention, the reservoir, pump and valve(s) are contained within a flat member, which is integrally attached to the sleeve and which can be implanted underneath the patient's skin above and immediately adjacent to the penis.

The foregoing and other objects and advantages will become apparent from the drawings and description which follows:

BRIEF DESCRIPTION OF THE DRAWINGS

FIG. 4 is a perspective view, partly in section, showing the embodiment of FIG. 1 positioned for implantation;

FIG. 5 is a perspective view, partly in section, showing the implant of FIG. 1 in place; and FIG. 6 is a cross sectional view taken along the line 6—6 in FIG. 5.

DESCRIPTION OF THE PREFERRED EMBODIMENTS

Figure 1:
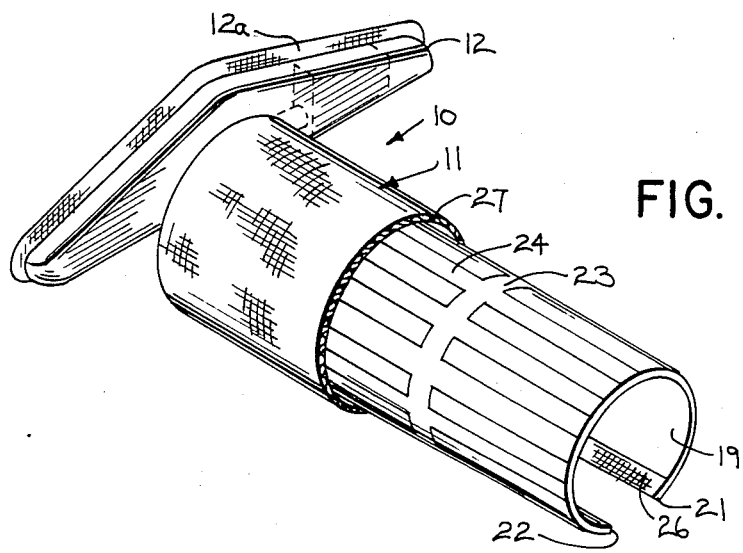
FIG. 1 is a perspective view, partly in section, of the preferred embodiment of the penile erectile system of the present invention.
Figure 2:
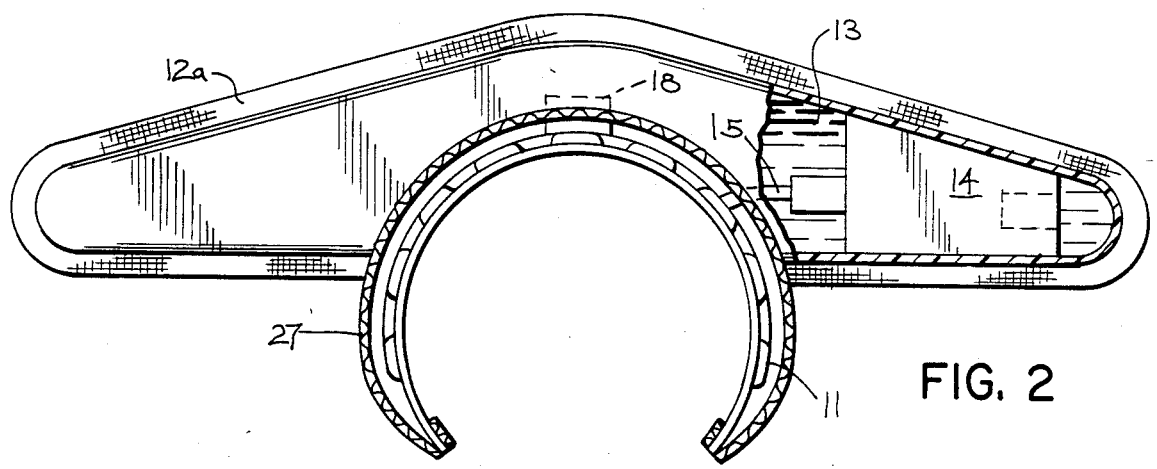
FIG. 2 is a front view, partly in section, of the implant of FIG. 1.
Figure 3:
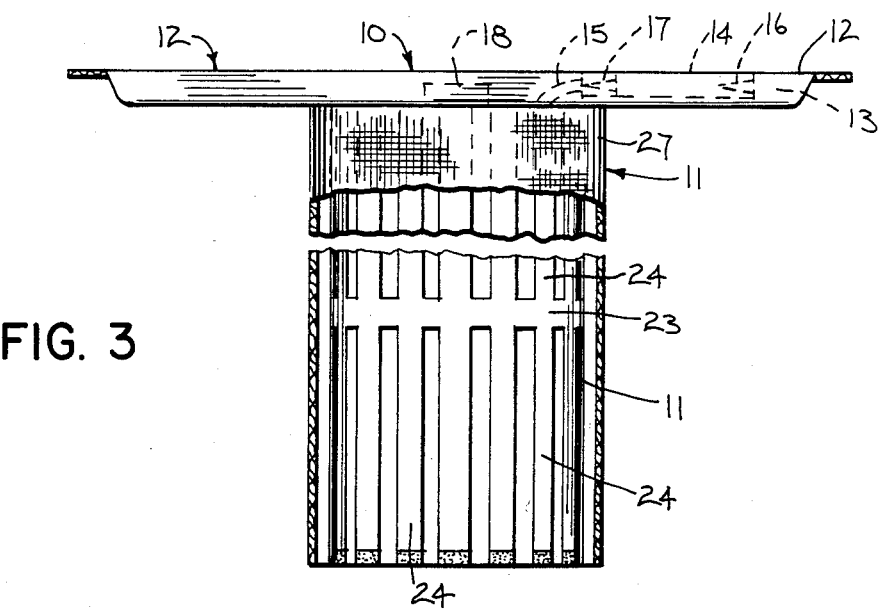
FIG. 3 is a top view, partly in section, of the implant of FIG. 1.

Referring now to FIGS. 1 to 3, the preferred embodiment of the penile erectile system 10 is seen to comprise a sleeve 11 and a body member 12 which contains a reservoir 13, a pump 14 and a passageway 15, seen best in FIGS. 2 and 3, leading from the pump 14 to the sleeve 11.

Turning to FIG. 3, it can be seen that the pump 14 has a pair of check valves 16 and 17. Both the inlet check valve 16 which controls flow of fluid into the pump 14 from the reservoir 13 and the outlet check valve 17 which controls flow from the pump 14 to the passageway 15 may be duck bill type valves. As seen in FIGS. 2 and 3, the body member 12 also includes a relief valve 18 controlling fluid flow from the sleeve 11 to the reservoir 13. The relief valve 18 is of the type which opens when squeezed or if the pressure in the sleeve exceeds a safe operating level.

As seen best in FIGS. 3 and 6, the main body of the sleeve 11 is comprised of an inner wall 19 and an outer wall 20 which are sealed together at their edges 21, 22, and at points 23 within their borders to form a plurality of longitudinally divided chambers 24 seen in FIGS. 1 to 4. The chambers 24 are interconnected by a manifold (not shown) so that they are all pressurized when the pump 14 is squeezed.

Referring to FIGS. 1 and 4, it can be seen that suturing strips 26 are attached to the inner wall 19 of the sleeve 11 adjacent the edges 21 and 22. The suturing strips 26 can be used to anchor the sleeve 11 in place. Instead of the suturing strips the edges 21 and 22 can be connected with a membrane (not shown) to keep the sleeve in place. The body 22 is also provided with similar suturing strip 12a.

In the preferred embodiment, the inner wall 19 of the sleeve 11 is of a relatively inelastic material and the outer wall 20 is more elastic. Thus, when the chambers 24 in the sleeve 11 are pressurized the outer wall 20 will stretch or distend to increase the penile girth. The inelastic inner wall 19 however, will not stretch and exert excessive pressure on the penis. The inner wall 19 may be made relatively inelastic by making it thicker than the outer wall 20 or using as the material of the inner wall 19 a silicone coated mesh or woven fabric of limited distensibility. The outer wall 20 may be of relatively thin silicone rubber which is quite elastic or of a material of controlled elasticity, such as the silicone rubber coated mesh fabric shown in U.S. Pat. No. 4,201,202. The sleeve 11 preferably is encased in a smooth outer cover 27 of elastic material, such as silicone rubber, or controlled elasticity such as silicone coated mesh.

The necessary seals between the walls 19 and 20 of the sleeve, and between the various components of the system may be made using a suitable adhesive or by other suitable means.

Once the system 10 is implanted and is in its nonpressurized state, the flexible sleeve 11 permits the penis to assume a substantially normal, flaccid position. However, when the chambers 24 of the sleeve 11 are pressurized the sleeve 11 becomes rigid and the penis assumes an erectile position.

The valves 16 and 17, which control the flow of fluid into and from the pump 14 are preferably normally closed valves which may be opened by manually squeezing the pump 14. A suitable valve is the well known duck bill valve. However, other valves including those disclosed in U.S. Pat. No. 4,369,771 can be used.

The relief valve 18 is one that will open if the pressure in the chambers 24 of the sleeve 11 exceeds a safe level, and automatically close when the excessive pressure has been relieved. The relief valve feature also makes it possible to quickly depressurize the sleeve by exerting a strong squeezing force on the penis. A suitable valve with a relief valve feature is shown in U.S. Pat. No. 4,364,379.

In a preferred embodiment of the implant of the present invention, the reservoir 13, pump 14, passageway 15 and the chambers 24, even when nonpressurized, are substantially filled with pressurizing fluid. Thus, the amount of fluid needed to competely fill, pressurize and rigidize the chambers 24 is minimal. As a result, the pump 14 can be relatively small in size, approximately 10 to 15 cc in volume, and thus, can be conveniently and inconspicuously implanted beneath the patient's skin in the abdominal region immediately above the penis.

The term "substantially filled" as used herein to describe the fluid content of a chamber means that a chamber contains about 60% to about 95% or more of its capacity of a noncompressible fluid such as water, saline or a free flowing gel. The actual content of fluid can vary; however, the implant when "substantially filled" should be still sufficiently flexible so that the penis can assume a normal flaccid position.

The body member 12 which is of flexible resilient material can be provided with one or more small, integral resealable ports of valves (not shown), if desired, so that additional fluid can be added to the closed system with a hypodermic needle after the system has been implanted. A suitable resealable valve is disclosed in U.S. Pat. No. 3,919,724.

All of the parts and components of the prosthesis are preferably made of or covered with medical grade silicone rubber which is non-reactive, non-toxic and well tolerated by the adjacent organic tissues. Silicon rubber is preferred because it is quite resistant to wear and remains functional for long periods of time. However, other suitable materials, such as a polyurethane, possessing the desired properties may also be employed.

The surgical procedure for implanting the embodiment of FIG. 1 is quite simple. The penile shaft is exposed and an incision made in the abdominal skin as seen in FIG. 4. The sleeve is positioned around the penile shaft and the edges are then sutured to each other using the non-absorbable suture strips and sutures. The body member 12 at proximal end of the implant is sutured in place using suture strip 12a and the distal end of the sleeve inserted between the tip of the corporae and the glans after undermining a clevage between them. The distal end of the implant will then be sutured to the tunica albuginea of the corpus. In this way both ends of the implant will be fixed to both ends of the penis and when inflated it will stretch the penile shaft in all its length. The implanted system is shown in FIG. 6.

It will be apparent to those skilled in the art that the penile erectile system of the present invention possesses several unique advantages. One advantage is that the superficial site of the implanted sleeve makes possible the early diagnosis of any leaks or deformities. Another advantage is that the system leaves intact the spongy tissues in the corpora cavornosa of the patient, thus both creating the possibility of using the system as an adjunct in the treatment in psychogenic impotents and making the operation reversible. In such cases, when the patient can achieve a normal erection, the system can be taken out easily without leaving an important scar. Still another advantage of the system is that it may be implanted as an adjunct in elderly men that cannot achieve full erections, as well as in men who have had a total loss of their ability to have an erection for various reasons, including spinal cord injury patients.

It is to be understood that the foregoing description has been for purposes of illustration and that a number of modifications and changes may be made without departing from the spirit and scope of the present invention. For example, the sleeve and body member may be made in other shapes and sizes than those shown and described and other pumps and valves can be used. Therefore, it is to be understood that the invention is not to be limited by any of the specific embodiments described but only by the claims which follow:

We claim:

1. A penile implant for treating impotency in a male patient, said implant comprising:
   (a) a sleeve of biocompatible material for implanting about a penile shaft beneath the penile skin, between the shaft and the skin, said sleeve having at least one pressurizable chamber; and
   (b) a relatively flat body member for implanting beneath the patient's skin in the abdominal region immediately above the penis, said body member being attached to one end of said sleeve and containing therewithin pressurizing means for pressurizing said chamber to make it rigid, said means comprising a fluid reservoir for pressurizing fluid, a pump, and valve means for controlling the flow of fluid between the pressurizing means and the pressurizing chamber.

2. An implant of claim 1 in which the valve means contains an excess pressure relief feature which causes it to automatically open when the fluid pressure in the chamber exceeds a predetermined safe level.

3. An implant of claim 1 in which the sleeve has a plurality of interconnected chambers.

4. An implant of claim 1 in which the sleeve is provided with anchoring means for securing it in place about the penile shaft.

5. An implant of claim 1 in which said sleeve includes apertures for the ingrowth of tissue to anchor the sleeve in place.

6. An implant of claim 1 in which said chamber of the sleeve has a first relatively inelastic inner wall and a second relatively elastic outer wall.

7. An implant of claim 1 in which the implant is a closed system which includes resealable means for introducing or withdrawing pressurizing fluid.

8. A method of surgically treating erectile impotency in a patient, said method comprising: implanting an implant of claim 1 in the patient with the sleeve about the penile shaft under the penile skin and the flat body member beneath the patient's skin in the abdominal region above the penis.

* * * * *